(12) United States Patent
Uyama et al.

(10) Patent No.: US 11,052,030 B2
(45) Date of Patent: Jul. 6, 2021

(54) METHOD FOR MANUFACTURING MICROEMULSION-TYPE COSMETIC

(71) Applicant: SHISEIDO COMPANY, LTD., Tokyo (JP)

(72) Inventors: Makoto Uyama, Yokohama (JP); Reiji Miyahara, Yokohama (JP)

(73) Assignee: SHISEIDO COMPANY, LTD., Tokyo (JP)

(*) Notice: Subject to any disclaimer, the term of this patent is extended or adjusted under 35 U.S.C. 154(b) by 0 days.

(21) Appl. No.: 16/576,229

(22) Filed: Sep. 19, 2019

(65) Prior Publication Data

US 2020/0009036 A1   Jan. 9, 2020

Related U.S. Application Data

(62) Division of application No. 15/762,813, filed as application No. PCT/JP2016/076128 on Sep. 6, 2016, now abandoned.

(30) Foreign Application Priority Data

Sep. 29, 2015   (JP) .................................. 2015-191487

(51) Int. Cl.
| A61K 8/58 | (2006.01) |
| A61K 8/31 | (2006.01) |
| A61K 8/06 | (2006.01) |
| A61K 8/891 | (2006.01) |
| A61K 8/89 | (2006.01) |
| A61K 8/39 | (2006.01) |
| A61Q 19/00 | (2006.01) |
| A61Q 5/00 | (2006.01) |
| A61K 8/34 | (2006.01) |
| A61K 8/86 | (2006.01) |

(52) U.S. Cl.
CPC ................ A61K 8/585 (2013.01); A61K 8/06 (2013.01); A61K 8/068 (2013.01); A61K 8/31 (2013.01); A61K 8/342 (2013.01); A61K 8/345 (2013.01); A61K 8/39 (2013.01); A61K 8/86 (2013.01); A61K 8/89 (2013.01); A61K 8/891 (2013.01); A61Q 5/00 (2013.01); A61Q 19/00 (2013.01); A61Q 19/007 (2013.01)

(58) Field of Classification Search
None
See application file for complete search history.

(56) References Cited

U.S. PATENT DOCUMENTS

| 5,449,510 | A * | 9/1995 | Gregoire ................ A61K 8/062 424/60 |
| 5,753,241 | A * | 5/1998 | Ribier .................... A61K 8/062 424/401 |
| 6,391,290 | B1 * | 5/2002 | Fowler .................... A61K 8/06 424/400 |
| 6,858,200 | B2 * | 2/2005 | Fowler .................... A61K 8/06 424/400 |
| 7,329,403 | B2 * | 2/2008 | Chuah ...................... A61K 8/26 424/65 |
| 2009/0252771 | A1 * | 10/2009 | Coccia .................... A61K 8/06 424/401 |
| 2010/0190871 | A1 | 7/2010 | Araki et al. |
| 2015/0190327 | A1 * | 7/2015 | Djedour ................... A61K 8/37 424/490 |
| 2015/0216787 | A1 | 8/2015 | Hori et al. |

FOREIGN PATENT DOCUMENTS

| EP | 2 777 690 | 9/2014 |
| JP | 2013-121947 | 6/2013 |
| JP | 2014-74058 | 4/2014 |
| WO | WO2013178752 | * 12/2013 |

OTHER PUBLICATIONS

PCT/JP2016/076128, Written Opinion and International Search Report, dated Oct. 25, 2016, 5 pages—English, 6 pages—Japanese.
EP 16851047.7, European Search Report dated Apr. 18, 2019, 7 pages—English.
Hydrophilic-Lipophilic Balance—an overview, ScientDirect, https://www.sciencedirect.com, pp. 1-10, from: Polar Lipids, 2015, dated Dec. 11, 2018.
"Mixing fine emulsions", NutriCos, published by B5 srl, www.b%srl.com, by Christine Banaszok, dated Sep./Dec. 2011, pp. 15-17.
Nikkol MGS-150V, (Glyceryl Stearate, PEG-60 Glycerty Stearate), dated Dec. 11, 2018, 1 page, https://www.chemical-navi.com/en/product_search/detail126.html.

* cited by examiner

*Primary Examiner* — Jennifer A Berrios
(74) *Attorney, Agent, or Firm* — Andrew F. Young, Esq.; Nolte Lackenbach Siegel

(57) ABSTRACT

A method of preparing a fine oil-in-water emulsion comprising an oil phase based on silicone and/or hydrocarbon oils, in which the oil phase particles have an average particle size of 150 nm or less. The emulsion is stabilized by a carboxy-modified silicone in combination with a C16 to 22 higher alcohol; a nonionic surfactant having a POE chain and an HLB of 5 to 10; and a dihydric glycol. The emulsions can be prepared without the use of a high-pressure emulsifying apparatus.

2 Claims, No Drawings

METHOD FOR MANUFACTURING MICROEMULSION-TYPE COSMETIC

CROSS REFERENCE TO RELATED APPLICATIONS

This application is a divisional of U.S. Ser. No. 15/762,813 filed on Mar. 23, 2018, the entire contents of which are incorporated herein fully by reference, which claims priority as a § 391 National Phase in the United States of international application No. PCT/JP2016/076128 filed Sep. 6, 2016, the entire contents of which is also incorporated full by reference, which in turn claims priority from Japanese Patent Application Serial No. 2015-191487 filed Sep. 29, 2015.

FIGURE SELECTED FOR PUBLICATION

None

FIELD OF THE INVENTION

The present invention relates to a fine emulsion-type cosmetic and a production method thereof, particularly to the preparation of surfactants therefor.

BACKGROUND

Of oil-in-water emulsion compositions, particularly, those having small-size oil droplets as the inner phase and exhibiting a transparent appearance are referred to as fine emulsions. When an oil agent is blended to a luxurious lotion or the like, the appearance of the cosmetic comprising such emulsion does not degrade, and thus, a commercially valuable cosmetic that combines an appearance having excellent transparency and the functionality and feeling in use of the oil agent can be provided.

These fine emulsions are generally produced by pulverizing emulsified particles of an emulsion with high shearing force using an emulsifying apparatus capable of applying high shearing force, such as high-pressure emulsifying apparatuses.

However, fine emulsion preparation by means of such a high-pressure emulsifying apparatus leads to an increase in the production cost, and treatment with high shearing force may causes deterioration in various functional raw materials.

Of such fine emulsions, a fine emulsion in thermodynamic equilibrium is referred to as a microemulsion.

PRIOR ART DOCUMENTS—PATENT LITERATURE

PTL 1—Japanese Unexamined Patent Publication No. 2014-74058

BRIEF DESCRIPTION OF THE INVENTION

The present invention has been made in view of the conventional art, and the problem to be solved is to provide a fine emulsion-type cosmetic comprising a finely-emulsified oil phase mainly based on a silicone oil or hydrocarbon oil without use of a high-pressure emulsifying apparatus.

Solution to Problem

The present inventors have made investigations to solve the problem and, as a result, found that use of a specific carboxy-modified silicone can easily provide a fine emulsion-type cosmetic, via a microemulsion phase in course of the process, having completed the present invention.

That is, a cosmetic, according to the present invention that is: a fine emulsion-type cosmetic having an average emulsion particle size of 150 nm or less and comprises: an aqueous phase that is a continuous layer; an oil phase dispersed in the aqueous phase that comprises at least 82% by mass of an oil consisting of a silicone oil and a hydrocarbon oil therein; a C16 to 22 higher alcohol; a nonionic surfactant having a POE chain and an HLB of 5 to 10; a dihydric glycol; and a carboxy-modified silicone represented by the following formula (1);

[Formula 1]

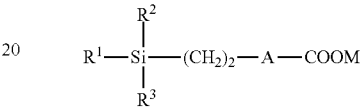

(1)

wherein R1 and R2 are respectively a functional group represented by —O—Si(R$^4$)$_3$ in which R$^4$ is an alkyl group having 1 to 6 carbon atoms; R$^3$ is a monovalent hydrocarbon group having 1 to 10 carbon atoms; M is a hydrogen atom, metal atom, or organic cation; A is a linear or branched alkylene group represented by C$_q$H$_{2q}$; and q is an integer of 6 to 20.

The mass ratio of the silicone to hydrocarbon oil in the oil phase is preferably 1:9 to 9:1.

In the cosmetic according to the present invention, the mass ratio of (oil agent)/(carboxy-modified silicone+higher alcohol+nonionic surfactant) is preferably 1.5 or less.

A method of producing a fine emulsion-type cosmetic according to the present invention comprising steps of; preparing a microemulsion by mixing the acid moiety of a carboxy-modified silicone represented by the formula (1), a higher alcohol, a nonionic surfactant, an oil phase, an organic amine and/or alkali metal, a portion of an aqueous phase, and dihydric glycol; and adding the rest of the aqueous phase to the microemulsion and diluting the microemulsion.

Advantageous Effects of Invention

The cosmetic according to the present invention, which contains a specific carboxy-modified silicone, a higher alcohol, and a nonionic surfactant, can easily become a fine emulsion composition without being carried out high-pressure emulsification or the like.

The above and other aspects, features and advantages of the present invention will become apparent from the following description read in conjunction with the accompanying drawings, in which like reference numerals designate the same elements.

BRIEF DESCRIPTION OF THE DRAWINGS

None

DETAILED DESCRIPTION OF THE PREFERRED EMBODIMENTS

Hereinafter, an example of the present invention will be described.

In the present invention,
[Carboxy-Modified Silicone]

The carboxy-modified silicone used in the present invention is a compound represented by the formula (1):

[Formula 1]

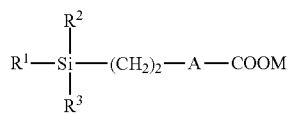
(1)

The carboxy-modified silicone represented by the formula (1) is a carboxy-modified silicone modified with an alkylcarboxyl group, characterized by containing a total of 2 to 20 silicon atoms on average per molecule.

In the formula (1), at least one of $R^1$ to $R^3$ is a functional group represented by $-O-Si(R^4)_3$ in which $R^4$ is either an alkyl group having 1 to 6 carbon atoms or a phenyl group. All of $R^1$ to $R^3$ may be either of the above functional groups. Alternatively, when at least one of $R^1$ to $R^3$ is the above functional group, the rest of $R^1$ to $R^3$ may be either substituted or unsubstituted monovalent hydrocarbon groups, which may be the same or different.

In the functional group represented by $-O-Si(R^4)_3$, $R^4$ is either an alkyl group having 1 to 6 carbon atoms or a phenyl group. Examples of the alkyl group having 1 to 6 carbon atoms include linear-chain, branched, or cyclic alkyl groups such as methyl, ethyl, n-propyl, i-propyl, n-butyl, i-butyl, s-butyl, pentyl, neopentyl, cyclopentyl, and hexyl. Examples of the functional group represented by $-O-Si(R^4)_3$ include $-O-Si(CH_3)_3$, $-O-Si(CH_3)_2(C_2H_5)$, $-O-Si(CH_3)_2(C_3H_7)$, $-O-Si(CH_3)_2(C_4H_9)$, $-O-Si(CH_3)_2(C_5H_{11})$, $-O-Si(CH_3)_2(C_6H_{13})$, and $-O-Si(CH_3)_2(C_6H_5)$. The functional group is preferably a trialkylsiloxy group, most preferably a trimethylsiloxy group.

When at least one of $R^1$ to $R^3$ in the formula (1) is the functional group represented by $-O-Si(R^4)_3$, the others of $R^1$ to $R^3$ may be either substituted or unsubstituted monovalent hydrocarbon groups, which may be the same or different. Examples of the unsubstituted monovalent hydrocarbon group as $R^1$ to $R^3$ include linear-chain, branched, or cyclic alkyl groups such as methyl, ethyl, n-propyl, i-propyl, n-butyl, i-butyl, s-butyl, pentyl, neopentyl, cyclopentyl, and hexyl; aryl groups such as phenyl, tolyl, and xylyl groups: and aralkyl groups. Examples of the substituted monovalent hydrocarbon group as $R^1$ to $R^3$ include perfluoroalkyl groups such as 3,3,3-trifluoropropyl and 3,3,4,4,4-pentafluorobutyl groups; aminoalkyl groups such as 3-aminopropyl and 3-(aminoethyl)aminopropyl groups; and amidoalkyl groups such as acetylaminoalkyl groups. A portion of the hydrocarbon group of $R^1$ to $R^3$ may be substituted with a hydroxyl group, alkoxy group, polyether group, or perfluoropolyether group. Examples of the alkoxy group include methoxy, ethoxy, and propoxy groups.

When one or two of $R^1$ to $R^3$ in the formula (1) is/are the functional group(s) represented by $-O-Si(R^4)_3$, the other(s) of $R^1$ to $R^3$ is/are preferably a linear-chain or branched alkyl group(s) having 1 to 6 carbon atoms, particularly preferably a methyl group(s) or ethyl group(s). Particularly, all or two of $R^1$ to $R^3$ in the formula (1) are preferably the functional groups represented by $-O-Si(R^4)_3$, and the other of $R^1$ to $R^3$ is preferably a methyl or ethyl group.

M is a hydrogen atom, metal atom, or organic cation. Examples of the metal atom include monovalent alkali metals, divalent alkali metals, and di- or higher valent metal atoms. Examples of the monovalent alkali metal include, Li, Na, and K, examples of the divalent alkali metal include Mg, Ca, and Ba, and other examples include Mn, Fe, Co, Al, Ni, Cu, V, Mo, Nb, Zn, and Ti. Examples of the organic cation include ammonium, monoethanolammonium, triethanolammonium, arginine-neutralized, and aminomethyl propanol (AMP)-neutralized ions. M is particularly preferably a hydrogen atom or monovalent alkali metal or may be a mixture thereof.

A is a linear-chain or branched-chain alkylene group represented by $C_qH_{2q}$, and q is an integer of 0 to 20. When q=0, the carboxy-modified silicone represented by the formula (1) is a compound represented by the following formula (1') (below), and the carboxyl-modified group is bonded with silicon via an ethylene group. In the present invention, q is preferably 2 to 15, more preferably 6 to 12. In contrast, when the value of q exceeds the upper limit, the feeling in use may be poor.

[Formula 1']

(1')

The carboxy-modified silicone represented by the formula (1) is characterized by containing a total of 2 to 20 silicon atoms on average per molecule. The carboxy-modified silicone contains preferably a total of 3 to 18 silicon atoms, particularly preferably a total of 3 to 7 silicon atoms on average.

The carboxy-modified silicone represented by the formula (1) that can be used preferably is more specifically a carboxy-modified silicone wherein $R^1$ and $R^2$ each are a functional group represented by $-O-Si(R^4)_3$ in which $R^4$ is an alkyl group having 1 to 6 carbon atoms; $R^3$ is a linear-chain or branched alkyl group having 1 to 6 carbon atoms; and q has a value of 6 to 12.

[Higher Alcohol Having 16 to 22 Carbon Atoms]

The monohydric aliphatic alcohol having 16 to 22 carbon atoms used in the present invention (hereinafter it is also referred to as a higher alcohol simply) is a saturated or unsaturated monohydric aliphatic alcohol. The alcohol can be either linear-chain or branched, more preferably linear-chain. Additionally, the alcohol is preferably a higher alcohol having a melting point of 40° C. or more. Examples of the higher alcohol having 16 to 22 carbon atoms used in the present invention include stearyl alcohol, isostearyl alcohol, oleyl alcohol, octyl dodecanol, chimyl alcohol, cetanol, cetostearyl alcohol, hexyl decanol, and behenyl alcohol. In the present invention, it is preferred that a higher alcohol having a melting point of 40 to 80° C. is singly used or a combination of a plurality of higher alcohols is used so as to achieve a melting point of 40 to 70° C.

An amount of the higher alcohol added is preferably 2 to 10% by mass, more preferably 3 to 8% by mass in the composition, in the stage of preparing the fine emulsion.

[Nonionic Surfactant]

A preferable nonionic surfactant used in the present invention has an HLB of 5 to 10, preferably an HLB of 6 to 9 and has a POE group.

Specific examples thereof include PEG-5 glyceryl stearate, POE (6) stearyl ether, POE (10) hydrogenated castor oil, and POE (20) hydrogenated castor oil.

An amount of the nonionic surfactant added is preferably 2 to 15% by mass, more preferably 5 to 10% by mass in the composition in the stage of preparing the fine emulsion.

[Dihydric Glycol]

Examples of the dihydric glycol used in the present invention include dipropylene glycol, ethylene glycol, diethylene glycol, propylene glycol, and 1,3-butylene glycol. The dihydric glycol is present preferably in an amount of 10 to 30% by mass, more preferably 15 to 25% by mass in the composition, in the stage of preparing the fine emulsion.

[Oil Agent]

The oil agent used as the oil phase of the present invention contains a silicone oil and a hydrocarbon oil.

Examples of the silicone oil include linear silicones such as dimethylpolysiloxane, methylphenylpolysiloxane, and methylhydrogenpolysiloxane; and cyclic silicones such as octamethylcyclotetrasiloxane, decamethylcyclopentasiloxane, and dodecamethylcyclohexasiloxane.

Examples of the hydrocarbon oil include liquid paraffin, squalane, squalene, paraffin, isoparaffin, and ceresin.

In the present invention, the silicone oil and the hydrocarbon oil constitute 82% by mass or more of the oil phase. When the oil phase contains 18% by mass or more of an oil other than silicone or hydrocarbon oils, such as an ester oil, it is difficult to prepare the fine emulsion.

The formulation amount of the oil phase blended in the step of preparing the fine emulsion preferably provides the ratio, oil agent/(carboxy-modified silicone+higher alcohol+nonionic surfactant), is 1.5 or less.

When the ratio exceeds 1.5, it may be difficult to prepare the fine emulsion. There is no particular lower limit on the amount of the oil agent blended. However, with respect to the properties of the fine emulsion, the amount thereof is preferably 10% by mass or more in the composition, in the stage of preparing the fine emulsion.

To the cosmetic of the present invention, in addition to the above essential components, other components usually used in the cosmetic or pharmaceutical, for example, oils, waxes, moisturizers, emulsifiers, surfactants, thickeners, gelling agents, metal soaps, water-soluble polymers, oil-soluble polymers, drugs, antioxidants, pigments, dyes, pearlescent agents, lame agents, organic/inorganic powders, and fragrances can be blended as needed, within a qualitative/quantitative range that does not impair the effects of the present invention.

The use application of the cosmetic of the present invention is not particularly limited, and the cosmetic is particularly preferably used in lotions with respect to its properties. In addition, the cosmetic can be also used in various cosmetics, for example, skin care cosmetics such as moisture cream, moisture milky lotion, moisture lotion, massage cream, massage lotion, and essence; hair care cosmetics such as hair cream, hair lotion, and hair dressing; body care cosmetics such as sun screen, body cream, and body lotion; make-up cosmetics such as lipstick, mascara, eye liner, nail enamel, liquid foundation, and gel foundation; and cleansers such as makeup remover, shampoo, rinse, and two-in-one shampoo.

The embodiment of the present invention will be described in detail hereinbelow.

First, the present inventors attempted to prepare the fine emulsion using various compositions.

Results are shown in Table 1.

TABLE 1

| | Test examples | 1-1 | 1-2 | 1-3 | 1-4 |
|---|---|---|---|---|---|
| Surfactant | Carboxy silicone | 1 | | | |
| | Stearic acid | | 1 | | 1 |
| | Oleic acid | | | 1 | |
| Stabilizer | Behenyl alcohol | 1.5 | 1.5 | 1.5 | 1.5 |
| | PEG-5 glyceryl stearate | 2.13 | 2.13 | 2.13 | 2.13 |
| Oil phase | Silicone oil | 2 | 2 | 2 | 2 |
| | Hydrocarbon oil | 2 | 2 | 2 | 2 |
| Aqueous phase | Ion-exchanged water | 7.8 | 7.8 | 7.8 | 7.8 |
| | Triethanolamine | 0.44 | 0.63 | 0.63 | 0.63 |
| | Dipropyleneglycol | 6 | 6 | 6 | 6 |
| Production method | Emulsifier | Henschel | Henschel | Henschel | high-pressure emulsifier |
| Evaluation | Appearance | one-phase | two-phase | two-phase | one-phase |

As shown in Table 1, an attempt to emulsify an oil phase was made using an anionic surfactant as the major surfactant, and additionally, a higher alcohol, a nonionic surfactant, and dihydric glycol.

That is, an oil agent together with the surfactant (acid moiety), higher alcohol, nonionic surfactant and dihydric glycol were dissolved and mixed at 80° C.

Then, an aqueous phase (at room temperature) in which an equivalent of triethanolamine as the counter ions of the surfactant was dissolved was added and mixed thereto, and the mixture was cooled. Then, the state of the phases was checked at 55 to 65° C.

As a result, test example 1-1 (present invention), in which a carboxy-modified silicone is used, provides a substantially transparent one-phase system. In the system when water is added, even though it is difficult to dissolve the silicone oil (polydimethylsiloxane 6CS) and hydrocarbon oil (olefin oligomer) therein, it is confirmed that a microemulsion is formed because a transparent one-phase system is provided.

In contrast, in test examples 1-2 and 1-3, an attempt to prepare an emulsion using a fatty acid (stearic acid or oleic acid) was made, but a white turbid two-phase system was obtained.

Meanwhile, in test example 1-4, when an attempt to prepare the fine emulsion of test example 1-2 (system in which stearic acid is used as the surfactant) using high-pressure emulsification, it was possible to prepare the emulsion.

In the system in which a carboxy-modified silicone is used as described above, it is understood that use of a specific higher alcohol, a nonionic surfactant, and dihydric glycol enables a microemulsion to be prepared by use of a usual mixing apparatus.

Additionally, the present inventors investigated the relation between the amount of the oil agent blended and other components. Results are shown in Table 2.

TABLE 2

| | Test examples | 2-1 | 2-2 | 2-3 | 1-1 | 2-4 | 2-5 | 2-6 |
|---|---|---|---|---|---|---|---|---|
| Surfactant | ① Carboxy silicone | 1 | 1 | 1 | 1 | 1 | 1 | 1 |
| Stabilizer | ② Behenyl alcohol | 1.5 | 1.5 | 1.5 | 1.5 | 1.5 | 1.5 | 1.5 |
| | ③ PEG-5 glyceryl stearate | 2.13 | 2.13 | 2.13 | 2.13 | 2.13 | 2.13 | 2.13 |
| Oil phas | ⑤ Silicone oil | 2 | 3 | 4 | 2 | 3 | 4 | 3 |
| | ⑥ Hydrocarbon oil | 2 | 3 | 4 | 2 | 3 | 3 | 4 |
| Aqueous | ⑦ Ion-exchanged water | 8.8 | 8.8 | 8.8 | 7.8 | 7.8 | 7.8 | 7.8 |
| phase | ⑧ Triethanolamine | 0.44 | 0.44 | 0.44 | 0.44 | 0.44 | 0.44 | 0.44 |
| | ④ Dipropylene glycol | 5 | 5 | 5 | 6 | 6 | 6 | 6 |
| The amount of oil agents blended/ Carboxy-modified silicone + higher alcohol + nonionic surfactant = ((⑤ + ⑥)/(① + ② + ③)) | | 0.86 | 1.3 | 1.73 | 0.86 | 1.3 | 1.51 | 1.51 |
| Evaluation | Appearance | one-phase | one-phase | two-phase | one-phase | one-phase | two-phase | two-phase |

As clearly seen from Table 2, it is understood that the amount of the oil agent blended closely relates to the amounts of the higher alcohol (behenyl alcohol), nonionic surfactant (PEG-5 glyceryl stearate), and carboxy-modified silicone and that an amount of the oil agent blended/ (carboxy-modified silicone+higher alcohol+nonionic sur factant) of 1.5 or less enables a good microemulsion to be prepared.

Then, the present inventors made an investigation into the relation between the type of the oil agent and microemulsion preparation. Results are shown in Table 3.

TABLE 3

| | Test examples | 2-2 | 3-1 | 3-2 | 3-3 | 3-4 | 3-5 | 3-6 | 3-7 | 3-8 |
|---|---|---|---|---|---|---|---|---|---|---|
| Surfactant | Carboxy silicone | 1 | 1 | 1 | 1 | 1 | 1 | 1 | 1 | 1 |
| Stabilizer | Behenyl alcohol | 1.5 | 1.5 | 1.5 | 1.5 | 1.5 | 1.5 | 1.5 | 1.5 | 1.5 |
| | PEG-5 glyceryl stearate | 2.13 | 2.13 | 2.13 | 2.13 | 2.13 | 2.13 | 2.13 | 2.13 | 2.13 |
| Oil phase | Silicone oil | 3 | 2 | 3 | 2 | 3 | 6 | — | 3 | 3 |
| | Octyl methoxycinnamate | — | 1 | 1 | — | — | — | — | — | — |
| | Bis-ethylhexyloxyphenol methoxyphenyltriazine | — | — | — | 1 | 1 | — | — | — | — |
| | Hydrocarbon oil | 3 | 3 | 2 | 3 | 2 | — | 6 | 1.8 | 2 |
| | Isohexadecyl isooctadecanoate | — | — | — | — | — | — | — | 1.2 | 1 |
| Aqueous | Ion-exchanged water | 7.8 | 7.8 | 7.8 | 7.8 | 7.8 | 7.8 | 7.8 | 7.8 | 7.8 |
| phase | Triethanolamine | 0.44 | 0.44 | 0.44 | 0.44 | 0.44 | 0.44 | 0.44 | 0.44 | 0.44 |
| | Dipropylene glycol | 6 | 6 | 6 | 6 | 6 | 6 | 6 | 6 | 6 |
| Evaluation | Appearance | one-phase | two-phase | two-phase | two-phase | two-phase | two-phase | two-phase | two-phase | one-phase |

As clearly seen from Table 3, coexistent of a polar oil such as so-called ester oil makes it extremely difficult to prepare a microemulsion, and a detailed investigation has revealed that the upper limit of such an oil in the oil agent is about 18% (see test examples 3-7 and 3-8).

Both the silicone oil and the hydrocarbon oil are required. In the case in which only one of them was used (test examples 3-5 and 3-6), it was difficult to prepare a good microemulsion.

Then, the present inventors made an investigation into the higher alcohol. Results are shown in Table 4.

TABLE 4

| | Test examples | 4-1 | 4-2 | 4-3 | 4-4 | 4-5 | 4-6 | 4-7 |
|---|---|---|---|---|---|---|---|---|
| Surfactant | Carboxy silicone | 1 | 1 | 1 | 1 | 1 | 1 | 1 |
| Stabilizer | Behenyl alcohol | 1.5 | — | — | — | — | — | — |
| | Deodorized cetanol | — | — | 1.5 | 1.3 | 1.2 | 1.1 | 1 |
| | PEG-5 glyceryl stearate | 2.13 | 2.13 | 2.13 | 2.13 | 2.13 | 2.13 | 2.13 |
| Oil phase | Silicone oil | 3 | 3 | 3 | 3 | 3 | 3 | 3 |
| | Hydrocarbon oil | 3 | 3 | 3 | 3 | 3 | 3 | 3 |
| Aqueous | Ion-exchanged water | 7.8 | 7.8 | 7.8 | 7.8 | 7.8 | 7.8 | 7.8 |
| phase | Triethanolamine | 0.3 | 0.3 | 0.3 | 0.3 | 0.3 | 0.3 | 0.3 |
| | Dipropyleneglycol | 6 | 6 | 6 | 6 | 6 | 6 | 6 |
| Evaluation | Appearance | one-phase | two-phase | one-phase | one-phase | one-phase | one-phase | one-phase |
| Second | Ion-exchanged water | 5 | 5 | 5 | 5 | 5 | 5 | 5 |
| aqueous | 1,3-butylene glycol | 5 | 5 | 5 | 5 | 5 | 5 | 5 |
| phase | Ion-exchanged water | 15 | 15 | 15 | 15 | 15 | 15 | 15 |
| Third | Ion-exchanged water | to 100 | to 100 | to 100 | to 100 | to 100 | to 100 | to 100 |
| aqueous | Glycerin | 1 | 1 | 1 | 1 | 1 | 1 | 1 |

TABLE 4-continued

|  | Test examples | 4-1 | 4-2 | 4-3 | 4-4 | 4-5 | 4-6 | 4-7 |
|---|---|---|---|---|---|---|---|---|
| phase | Ethanol (95%) | 3 | 3 | 3 | 3 | 3 | 3 | 3 |
|  | Phenoxyethanol | 0.5 | 0.5 | 0.5 | 0.5 | 0.5 | 0.5 | 0.5 |
|  | EDTA-2Na•2H$_2$O | 0.03 | 0.03 | 0.03 | 0.03 | 0.03 | 0.03 | 0.03 |
| Evaluation | Particle size (nm) | 106 | ~5 μm | 109 | 103 | 98 | 93 | 87 |
|  | PDI | 0.102 | — | 0.077 | 0.1 | 0.122 | 0.117 | 0.133 |
|  | pH | 8.24 | 8.23 | 8.17 | 8.26 | 8.26 | 8.25 | 8.2 |

In the present test, the microemulsion obtained as the similar manner, a second aqueous phase, and a third aqueous phase was added for dilution to prepare a lotion-type composition.

As clearly seen from Table 4, behenyl alcohol and deodorized cetanol exhibited substantially similar behavior. It is understood that the amount of the higher alcohol blended is variable unless the relation with the amount of the oil agent blended fails. When the particle size of oil droplets in the final lotion-type composition was measured, the average particle size was around 100 nm. Thus, the composition was confirmed to be a fine emulsion.

Subsequently, the present inventors prepared lotion-type compositions using various nonionic surfactants and evaluated the compositions. Results are shown in Table 5.

TABLE 5

|  | Test examples | 5-1 | 5-2 | 5-3 | 5-4 | 5-5 | 5-6 | 5-7 | 5-8 |
|---|---|---|---|---|---|---|---|---|---|
| Surfactant | Carboxy silicone | 1 | 1 | 1 | 1 | 1 | 1 | 1 | 1 |
| Stabilizer | Behenyl alcohol | 1.5 | 1.5 | 1.5 | 1.5 | 1.5 | 1.5 | 1.5 | 1.5 |
|  | PEG-5 glyceryl stearate (HL88) | — | 2.13 | — | — | — | — | — | — |
|  | Glyceryl monostearate (HLB5) | — | — | 2.13 | — | — | — | — | — |
|  | Batyl alcohol (HLB5) | — | — | — | 2.13 | — | — | — | — |
|  | POE (6)stearyl ether (HLB8) | — | — | — | — | 2.13 | — | — | — |
|  | POE(10)behenyl ether (HLB10) | — | — | — | — | — | 2.13 | — | — |
|  | POE(10)hydrogenated castor oil (HLB7) | — | — | — | — | — | — | 2.13 | — |
|  | POE(20)hydrogenated castor oil (HLB9) | — | — | — | — | — | — | — | 2.13 |
| Oil phase | Silicone oil | 3 | 3 | 3 | 3 | 3 | 3 | 3 | 3 |
|  | Hydrocarbon oil | 3 | 3 | 3 | 3 | 3 | 3 | 3 | 3 |
| Aqueous phase | Ion-exchanged water | 7.8 | 7.8 | 7.8 | 7.8 | 7.8 | 7.8 | 5 | 5 |
|  | Triethanolamine | 0.37 | 0.37 | 0.37 | 0.37 | 0.37 | 0.37 | 0.37 | 0.37 |
|  | Dipropylene glycol | 6 | 6 | 6 | 6 | 6 | 6 | 6 | 5 |
| Evaluation | Appearance | two-phase | one-phase | two-phase | two-phase | one-phase | two-phase | one-phase | one-phase |
| Second aqueous phase | Ion-exchanged water | 20 | 20 | 20 | 20 | 20 | 20 | 20 | 20 |
|  | 1,3-butylene glycol | 5 | 5 | 5 | 5 | 5 | 5 | 5 | 5 |
| Third aqueous phase | Ion-exchanged water | to 100 | to 100 | to 100 | to 100 | to 100 | to 100 | to 100 | to 100 |
|  | Glycerin | 3 | 3 | 3 | 3 | 3 | 3 | 3 | 3 |
|  | Ethanol (95%) | 5 | 5 | 5 | 5 | 5 | 5 | 5 | 5 |
|  | Phenoxyethanol | 0.5 | 0.5 | 0.5 | 0.5 | 0.5 | 0.5 | 0.5 | 0.5 |
| Evaluation | Particle size (nm) | ~10 μm | 92 | ~1 μm | ~1 μm | 101 | ~1 μm | 112 | 135 |

As seen from Table 5, use of nonionic surfactants having a POE chain and having an HLB of 5 to 10, preferably 6 to 9 enables good microemulsions to be prepared.

Then, the present inventors made an investigation into dihydric glycol. Results are shown in Table 6.

TABLE 6

|  | Test examples | 6-1 | 6-2 | 6-3 | 6-4 | 6-5 | 6-6 |
|---|---|---|---|---|---|---|---|
| Surfactant | Carboxy silicone | 1 | 1 | 1 | 1 | 1 | 1 |
| Stabilizer | Behenyl alcohol | 1.5 | 1.5 | 1.5 | 1.5 | 1.5 | 1.5 |
|  | PEG-5 glyceryl stearate (HLB8) | 2.13 | 2.13 | 2.13 | 2.13 | 2.13 | 2.13 |
| Oil phase | Silicone oil | 3 | 3 | 3 | 3 | 3 | 3 |
|  | Hydrocarbon oil | 3 | 3 | 3 | 3 | 3 | 3 |
| Aqueous phase | Ion-exchanged water | 7.8 | 7.8 | 7.8 | 5.6 | 6.6 | 7.8 |
|  | Triethanolamine | 0.37 | 0.37 | 0.37 | 0.37 | 0.37 | 0.37 |
|  | Dipropylene glycol | — | 1 | 6 | — | — | 10 |
|  | Propylene glycol | — | — | — | 5 | — | — |
|  | 1,3-butylene glycol | — | — | — | — | 5 | — |
| Evaluation | Appearance | two-phase | two-phase | one-phase | one-phase | one-phase | two-phase |
| Second aqueous phase | Ion-exchanged water | 20 | 20 | 20 | 20 | 20 | 20 |
|  | 1,3-butylene glycol | 5 | 5 | 5 | 5 | 5 | 5 |

TABLE 6-continued

| | Test examples | 6-1 | 6-2 | 6-3 | 6-4 | 6-5 | 6-6 |
|---|---|---|---|---|---|---|---|
| Third aqueous phase | Ion-exchanged water | to 100 | to 100 | to 100 | to 100 | to 100 | to 100 |
| | Glycerin | 3 | 3 | 3 | 3 | 3 | 3 |
| | Ethanol (95%) | 5 | 5 | 5 | 5 | 5 | 5 |
| | Phenoxyethanol | 0.5 | 0.5 | 0.5 | 0.5 | 0.5 | 0.5 |
| Evaluation | Particle size (nm) | — | ~3 μm | 92 nm | 98 nm | 93 nm | ~3 μm |

As clearly seen from Table 6, blending of dihydric glycol is useful for preparing a good microemulsion, but it is not possible to obtain a microemulsion in a range such that the content of dihydric glycol exceeds 30% by mass in the step of microemulsion preparation.

However, the second aqueous phase and the third aqueous phase are intended to dilute and disperse the microemulsion. Thus, addition of dihydric glycol or the like to the second aqueous phase or the third aqueous phase would not adversely affect the state of the microemulsion.

Subsequently, the present inventors made an investigation into the counter ions and degree of neutralization of the carboxy-modified silicone. Results are shown in Tables 7 and 8.

As clearly seen from Tables 7 and 8, as the counter ions of the carboxy-modified silicone, an organic amine (triethanolamine), alkali metal (potassium), or the like can be employed as similar to common fatty acid soaps. The degree of neutralization is not required to be 100%. Accordingly, the pH required for the product can be prioritized upon preparation.

Specific Examples of the present invention will be described hereinbelow.

TABLE 7

| | Test examples | 7-1 | 7-2 | 7-3 | 7-4 | 7-5 |
|---|---|---|---|---|---|---|
| Surfactant | Carboxy silicone | 1 | 1 | 1 | 1 | 1 |
| Stabilizer | Behenyl alcohol | 1.5 | 1.5 | 1.5 | 1.5 | 1.5 |
| | PEG-5 glyceryl stearate | 2.13 | 2.13 | 2.13 | 2.13 | 2.13 |
| Oil phase | Silicone oil | 3 | 3 | 3 | 3 | 3 |
| | Hydrocarbon oil | 3 | 3 | 3 | 3 | 3 |
| Aqueous phase | Ion-exchanged water | 7.8 | 7.8 | 7.8 | 7.8 | 7.8 |
| | Triethanolamine | 0.44 | 0.4 | 0.37 | 0.33 | 0.29 |
| | Dipropylene glycol | 6 | 6 | 6 | 6 | 6 |
| Second aqueous phase | Ion-exchanged water | 25 | 25 | 25 | 25 | 25 |
| Third aqueous phase | Ion-exchanged water | to 100 | to 100 | to 100 | to 100 | to 100 |
| | Glycerin | 3 | 3 | 3 | 3 | 3 |
| | Ethanol (95%) | 5 | 5 | 5 | 5 | 5 |
| | Phenoxyethanol | 0.5 | 0.5 | 0.5 | 0.5 | 0.5 |
| Evaluation | Degree of neutralization | 120 | 110 | 100 | 90 | 80 |
| | Particle size (nm) | 92 | 90 | 96 | 94 | 86 |
| | pH | 8.4 | 8.23 | 8.12 | 8.11 | 8.1 |

TABLE 8

| | Test examples | 8-1 | 8-2 | 8-3 | 8-4 | 8-5 |
|---|---|---|---|---|---|---|
| Surfactant | Carboxy silicone | 1 | 1 | 1 | 1 | 1 |
| Stabilizer | Behenyl alcohol | 1.5 | 1.5 | 1.5 | 1.5 | 1.5 |
| | PEG-5 glyceryl stearate | 2.13 | 2.13 | 2.13 | 2.13 | 2.13 |
| Oil phase | Silicone oil | 3 | 3 | 3 | 3 | 3 |
| | Hydrocarbon oil | 3 | 3 | 3 | 3 | 3 |
| Aqueous phase | Ion-exchanged water | 7.8 | 7.8 | 7.8 | 7.8 | 7.8 |
| | Potassium hydroxide | 0.16 | 0.15 | 0.14 | 0.12 | 0.11 |
| | Dipropylene glycol | 6 | 6 | 6 | 6 | 6 |
| Evaluation | Appearance | one-phase | one-phase | one-phase | one-phase | one-phase |
| Second aqueous phase | Ion-exchanged water | 25 | 25 | 25 | 25 | 25 |
| Third aqueous phase | Ion-exchanged water | to 100 | to 100 | to 100 | to 100 | to 100 |
| | Glycerin | 3 | 3 | 3 | 3 | 3 |
| | Ethanol (95%) | 5 | 5 | 5 | 5 | 5 |
| | Phenoxyethanol | 0.5 | 0.5 | 0.5 | 0.5 | 0.5 |
| Evaluation | Degree of neutralization | 120 | 110 | 100 | 90 | 80 |
| | Particle size (nm) | 83 | 87 | 96 | 111 | 145 |
| | pH | 9.52 | 9.47 | 9.46 | 9.43 | 9.38 |

EXAMPLE 1

[Translucent Lotion]

| Components to be blended | % by mass |
|---|---|
| 1. Purified water | balance |
| 2. EDTA-2Na•2H$_2$O | 0.03 |
| 3. Glycerin | 1.0 |
| 4. Ethanol | 3.0 |
| 5. Phenoxyethanol | 0.5 |
| 6. Carboxydecyl trisiloxane | 0.6 |
| 7. Cetanol | 0.66 |
| 8. PEG-5 glyceryl stearate | 1.28 |
| 9. Dipropylene glycol | 3.6 |
| 10. Polydimethylsiloxane 6CS | 1.8 |
| 11. Hydrogenated polydecene | 1.8 |
| 12. Triethanolamine | 0.18 |
| 13. Buthylene glycol | 5.0 |
| 14. Dipropylene glycol | 2.4 |

<Production Method>
(1): Components 1 to 5 are mixed at 25° C. for dissolution.
(2): Components 6 to 11 are dissolved and mixed at 70° C.
(3): A portion of component 1 together with component 12 is added to (2), and the mixture is mixed under stirring.
(4): A portion of component 1 together with component 13 and component 14 is mixed at 25° C. for dissolution.
(5): (4) is added to (3), and the mixture is mixed under stirring.
(6): (5) is added to (1), and the mixture is mixed under stirring.

The obtained lotion contains emulsified particles of 71 nm and provides a pH of 8.07 and an L value of 66.

EXAMPLE 2

[Translucent Lotion]

| Components to be blended | % by mass |
|---|---|
| 1. Purified water | balance |
| 2. EDTA-2Na•2H$_2$O | 0.03 |
| 3. Glycerin | 1.0 |
| 4. Ethanol | 3.0 |
| 5. Phenoxyethanol | 0.5 |
| 6. Carboxydecyl trisiloxane | 0.6 |
| 7. Cetanol | 0.66 |
| 8. PEG-5 glyceryl stearate | 1.28 |
| 9. Dipropylene glycol | 3.6 |
| 10. Polydimethylsiloxane 6CS | 1.8 |
| 11. Hydrogenated polydecene | 1.8 |
| 12. Triethanolamine | 0.18 |
| 13. Buthylene glycol | 5.0 |
| 14. Dipropylene glycol | 2.4 |

<Production Method>
(1): Components 1 to 5 are mixed at 25° C. to dissolution.
(2): Components 6 to 11 are dissolved and mixed at 70° C.
(3): A portion of component 1 together with component 12 is added to (2), and the mixture is mixed under stirring.
(4): A portion of component 1 together with component 13 and component 14 is mixed at 25° C. to dissolution.
(5): (4) is added to (3), and the mixture is mixed under stirring.
(6): (5) is added to (1), and the mixture is mixed under stirring.
The obtained lotion contains emulsified particles of 71 nm and provides a pH of 8.07 and an L value of 66.

Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

We claim:

1. A method of preparing a fine oil-in-water emulsion, comprising mixing together a first aqueous phase comprising:
   a) water;
   b) triethanolamine or potassium hydroxide; and
   c) 10 to 30% by mass, relative to the total mass of the fine oil-in-water emulsion, of a dihydric glycol;
      wherein the dihydric glycol is selected from the group consisting of dipropylene glycol, ethylene glycol, diethylene glycol, propylene glycol, and 1,3-butylene glycol;
with a mixture comprising
   d) an oil phase comprising at least 82% by mass of a combination of silicone oil and hydrocarbon oil;
   e) a carboxy-modified silicone;
   f) 2 to 10% by mass, relative to the total mass of the fine oil-in-water emulsion, of a higher alcohol having 16 to 22 carbon atoms; and
   g) a nonionic surfactant having a POE chain and an HLB of 5 to 9 in an amount of 5 to 10% by mass of the composition relative to the total mass of the fine oil-in-water emulsion;
      wherein an oil-in-water emulsion is formed following the mixing of components a)-g); and subsequently:
   h) diluting the resulting oil-in-water emulsion with a second aqueous phase, until a stable fine oil-in-water emulsion is produced, in which the oil phase particles have an average size of 150 nm or less;
wherein the carboxy-modified silicone has structure (1)

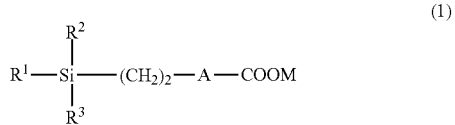

where each of R$^1$ and R$^2$ has the structure —O—Si(R$^4$)$_3$ in which R$^4$ is an alkyl group having 1 to 6 carbon atoms; R$^3$ is a monovalent hydrocarbon group having 1 to 10 carbon atoms; M is a hydrogen atom; A is a linear or branched alkylene group represented by (C$_q$H$_{2q}$); and q is an integer from 6 to 20;
where the mass ratio of (the oil phase)/(the higher alcohol, the nonionic surfactant and the carboxy-modified silicone) is 1.5 or less;
wherein the mixing step is conducted without the use of a high-pressure or high-shearing-force emulsifying apparatus; and
wherein the fine oil in water emulsion is visually a one phase system.

2. The method according to claim 1, wherein the mass of dihydric glycol is 15 to 25% of the total mass of the emulsion.

* * * * *